United States Patent [19]

Statland et al.

[11] 4,233,032

[45] Nov. 11, 1980

[54] FETAL LUNG MATURITY TEST

[75] Inventors: Bernard E. Statland, Sacramento, Calif.; Geoffrey Sher, Reno, Nev.

[73] Assignee: University of North Carolina at Chapel Hill, Chapel Hill, N.C.

[21] Appl. No.: 11,253

[22] Filed: Feb. 12, 1979

[51] Int. Cl.$^3$ ................ G01N 33/48; G01N 13/00
[52] U.S. Cl. ................ 23/230 B; 73/60.1; 422/61
[58] Field of Search .......... 23/230 B; 128/632, 636, 128/760, 771; 422/61; 73/60.1

[56] References Cited

PUBLICATIONS

J. A. Clements et al., New England Journal of Medicine, 286 (20), 1077–1081 (1972).
"Nonionic Surfactants", Martin J. Schick, ed., 505, Marcel Dekker, Inc., New York, 1967.
J. Edwards and P. Baillie, S. Afr. Med. J., 47, 2070–2073 (1973).
Geoffrey Sher, Bernard E. Statland and Dennis E. Freer, Abstract entitled "The Use of Graded Ethanol Volume Fractions in Assessing the Functionality of Surfactant in Amniotic Fluid", presented annual meeting of the Society of Gynecological Investigation; Atlanta, Georgia, Mar. 15–18, 1978.

*Primary Examiner*—Sidney Marantz
*Attorney, Agent, or Firm*—Bertram I. Rowland

[57] ABSTRACT

A simple rapid STAT test and test kit are provided for the reliable determination of prenatal lung maturity as well as other surfactant lipid dependent determinations. The method involves a shake test employing a plurality of vials having graduated volumes of ethanol, including a dye, normally in combination with a positive control. A predetermined amount of the sample is introduced into each of the vials, the vials shaken in a reproducible manner, and the highest ethanol volume fraction which provides for a stable foam determined. Based on statistical evaluations, an ethanol volume fraction above 0.45 will generally be regarded as positive, meaning healthy lung maturity, while a value below about 0.45 will generally indicate that further investigation is warranted.

6 Claims, No Drawings

FETAL LUNG MATURITY TEST

BACKGROUND OF THE INVENTION

1. Field of the Invention

Hyaline membrane disease is caused in part by inadequate synthesis of surface-tension lowering material (surfactant) by the lung. The neonatal hyaline membrane disease represents a major cause of perinatal mortality. It is therefore desirable to have a simple and rapid test which would permit a determination of lung maturity by determining surfactant lipid presence in amniotic fluid, the results of which would provide a reliable indication of the neonatal pulmonary maturity. Desirably, the test should be simple, rapid, and provide results which are easy to interpret.

2. Description of the Prior Art

In 1972, Clements and co-workers introduced the amniotic fluid foam stability test for assessing fetal pulmonary maturity. Clements, et al., *N.E.J.M.* 286, 1077 (1972). The test employed a 0.475 ethanol volume fraction in a 1:1 volume ratio of amniotic fluid and 95% ethanol. In 1973, Edwards and Baillie modified the Clements' test to provide for 50 volume percent ethanol with a 1:1 ratio of amniotic fluid and 100% ethanol. Edwards and Baillie, *S. Afr. Med. J.* 47, 2070 (1973). Both the Clements and Edwards and Baillie tests rely on combining the ethanol with a predetermined amount of the amniotic fluid, shaking the mixture, and observing whether a stable foam is obtained. The two tests have received mixed reviews in the literature and there have been differences as to the reliability of the tests. See, for example, Myers et al., *Am. J. Obstet. Gynecol.* 121, 961 (1975); Statland et al., *Am. J. Clin. Pathol.* 69, 514 (1978).

The subject invention has been described at an annual meeting of the Society of Gynecological Investigation; Atlanta, Ga., Mar. 15–18, 1978.

SUMMARY OF THE INVENTION

Detection of neonatal hyaline membrane disease (HMD) is provided by mixing a fixed predetermined volume of amniotic fluid with a plurality of vials containing graduated amounts of 95% aqueous ethanol, including the range from about 0.45 to about 0.5 volume fraction ethanol in the final mixture. A small amount of dye is added to the vials, and a control provided for comparison. The vials are all shaken in a reproducible manner and the highest ethanol volume fraction showing a stable foam is reported. A positive result is one that provides consistently stable foam in the vial initially containing 0.48 ethanol volume fraction or higher ethanolic content. The greater the amount of ethanol, the more difficult to obtain a stable foam. Absence of a stable foam in the 0.45 ethanol volume fraction vial suggests that further investigation be made to determine the neonatal pulmonary maturity.

DESCRIPTION OF THE SPECIFIC EMBODIMENTS

A rapid reliable simple assay is provided for determining fetal or neonatal pulmonary maturity through analysis of amniotic fluid. The method employs a plurality of vials having graduated amounts of ethanol including at least ethanol volume fractions in the range of 0.45 to 0.50 with graduations of 0.01 volume fractions when the ethanol is mixed with a predetermined amount of amniotic fluid. Additional volume fractions may be taken down to about 0.42 ethanol volume fraction.

Conveniently a kit is prepared having at least five vials with graduated volumes of 95% ethanol to provide the desired ethanol volume fractions upon addition of a fixed predetermined amount of amniotic fluid. In this way, the operator may use the same measuring device e.g. pipette or syringe, either manual or automatic, to measure the amniotic fluid volume accurately and repetitively. The amount of 95% ethanol employed in the vials should provide a range of at least 0.45 to 0.5 ethanol volume fractions in 0.01 gradations. The following table indicates the volume of 95% ethanol employed with 0.5 ml amniotic fluid, the resulting ethanol volume fraction and the volume ratio of 95% ethanol to amniotic fluid.

| Ethanol volume fraction | Volume of 95% ethanol (ml) | Volume ratio ethanol amniotic fluid |
|---|---|---|
| 0.42 | 0.395 | 0.790 |
| 0.43 | 0.415 | 0.830 |
| 0.44 | 0.430 | 0.860 |
| 0.45 | 0.450 | 0.900 |
| 0.46 | 0.470 | 0.940 |
| 0.47 | 0.490 | 0.980 |
| 0.48 | 0.510 | 1.02 |
| 0.49 | 0.530 | 1.06 |
| 0.50 | 0.550 | 1.10 |
| 0.51 | 0.580 | 1.16 |
| 0.52 | 0.605 | 1.21 |
| 0.53 | 0.630 | 1.26 |
| 0.54 | 0.660 | 1.32 |
| 0.55 | 0.685 | 1.37 |

In the range of particular interest 0.45 to 0.50 ethanol volume fraction, the ratios increase evenly by 0.040 fractions, from 0.900 to 1.10.

The serverity of the test increases with increasing ethanol volume fractions, due to both the increasing concentration of ethanol and the diminishing concentration of lipid surfactant.

A small amount of a compatible dye is employed, usually sufficient to enhance the visibility of foam bubbles at an interface. Preferably, a blue dye is employed, such as peacock blue dye.

In carrying out the method or preparing a kit, aqueous 95% ethanol is introduced into a plurality of vials, usually at least six vials and preferably seven vials. The amount of ethanol introduced should provide the desired graduations of ethanol volume percent, when a fixed amount of amniotic fluid is added. Usually, the amniotic fluid added will be relatively small, generally ranging from about 0.1 to 1 ml, preferably about 0.3 to 0.6 ml, and more preferred about 0.5 ml. Depending on the amount of amniotic fluid employed, the amount of 95% aqueous ethanol will be changed to maintain the same concentrations.

Before introducing the amniotic fluid into the ethanol containing vials, the amniotic fluid is first centrifuged. The supernatant is then collected and mixed by gentle inversion. Appropriate aliquots of the amniotic fluid are then dispensed into the previously prepared vials containing varying volumes of the ethanol/dye solution.

In addition to the five test vials, it is desirable to have two control vials. A positive control could be demonstrated by employing 40 microg. of dipalmitoyl lecithin in combination with an ethanol volume fraction of 0.43, by combining 40 microg. dipalmitoyl lecithin, 377 microl. of ethanol and 500 microl. of saline. For a negative control, a combination of 20 microg. of dipalmitoyl lecithin with 500 microl. of ethanol and 500 microl. of saline to provide an ethanol volume fraction of 0.50 could be employed. The same dye would be employed in the controls as employed in the test vials. There would then be a direct comparison between a negative control, a positive control and the test vials. Conveniently, the test kit vial would only contain the ethanolic solution of the dipalmitoyl lecithin, allowing a technician to introduce the predetermined amount of saline. In this manner, the measurement of the amniotic fluid and saline would be in the same way to minimize measurement variations by operators.

After adding the amniotic fluid and saline to the appropriate tubes, all the tubes are shaken vigorously for a predetermined time, preferably by a mechanical shaker to insure reproducible results. Only a short time is necessary, usually 30 secs. being satisfactory, but shorter or longer times may also be employed. After completion of shaking, a short period of time is allowed for the solution to settle and the test vials are compared to the control vials, with an uninterrupted ring of bubbles around the entire meniscus of the tube at the air-fluid interface interpreted as a positive result. Stable foam in excess of this amount is likewise interpreted as a positive result. A negative result is defined as the absence of stable foam or an amount of foam less than that required for the result to be interpreted as positive.

With a positive result (stable foam) indicating fetal lung maturity, 0.48 ethanol volume fraction has to date provided a 100% confidence level, while a positive result between 0.45 to 0.47 ethanol volume fraction has been slightly less than a 100% confidence level. Therefore, a positive result at ethanol volume fractions of 0.45 to 0.47 is indicative of a likelihood of fetal lung maturity.

While the above described test involves 95% ethanol, 100% ethanol could also be employed and the ratios modified, with different values employed for a positive or negative result. However, 95% ethanol is available and may be conveniently employed, and the results standardized with this reagent.

In order to demonstrate the subject invention, in a clinical assay, 14 tubes were prepard with varying amounts of 95% ethanol (0.395 ml–0.685 ml) to provide ethanol volume fractions ranging from 0.42 to 0.55. Into each of the vials was introduced 0.50 ml aliquots of amniotic fluid supernatant, so as to provide the final desired ethanol volume fraction gradations. After sealing the vials with air-tight plastic caps, the vials were vigorously shaken for a period of 30 secs. using a mechanical shaker. The persistence of an uninterrupted ring of foam at the fluid surface around the entire meniscus of the tube for longer than 15 secs. was interpreted as a "positive" result and the highest ethanol volume fraction capable of rendering such result was expressed as the Foam Stability Index (FSI). The following precautions were taken: amniotic fluid specimens contaminated with blood or meconium were discarded; amniotic fluid supernatant was gently mixed prior to performing the FSI-test to avoid layering of lipids; meticulous attention was given to accurate volumetric addition of both the amniotic fluid and ethanol reagent; and only an uninterrupted ring of bubbles at the fluid surface was interpreted as a "positive" result.

The majority of patients studied had complicated gestations and 33 of the infants born of these pregnancies were pre-term by pediatric aging and 18 had birth masses of less than 2.5 kg. An FSI-test was performed on each of the 59 patients included in the study. In 50 cases, a sufficient volume of amniotic fluid was available so as to allow the concurrent performance of the L/S ratio assay (Gluck et al. *Am. J. Obstet. Gynecol.* 109, 440–445 (1971). The respiratory status of the newborn was evaluated by a neonatologist who was unaware of the FSI-values. Infants were separated into three categories: (1) Hyaline Membrane Disease (HMD); (2) Transient Tachypnea of the Newborn (TTNB); and (3) no respiratory distress.

Of eight cases of HMD and TTNB, only one gave an FSI value above 0.45, this one example giving an FSI value of 0.47. Of the 51 patients showing no respiratory distress, only one had a FSI value below 0.45, and that value was 0.44. By comparison, the L/S ratio value, employing two as the cut-off, showed nine false HMD positive results and two false HMD negative results. Interestingly, the same patient, where the FSI value was positive for the presence of HMD was borderline in the L/S ratio.

The FSI-test can be employed in a number of ways for a number of purposes. It can be employed to follow the progressive attainment of fetal lung maturation sequentially in complicated or uncomplicated gestations; also, to evaluate the effectiveness of pharmacologic agents, administered to the mother or to the fetus, for the purposes of accelerating fetal lung maturation; to evaluate the effect of an altered intra-uterine environment on the developmental pattern of fetal biological maturity; to be used as a functional assay to quantitate the surface tension lowering ability of various phospholipids in biologic secretions; to evaluate the effect of parturition on the production and functionality of fetal/neonatal pulmonary surfactant.

The subject test has many advantages. As compared to prior shake tests, it is more quantitative in nature. The subject test provides a broad dynamic range which allows for greater reliability, as compared to the previous tests, which merely gave an unreliable yes or no answer. The subject test is capable of being performed rapidly, generally in approximately ten minutes and is therefore continuously available on a STAT basis. The test is relatively inexpensive and requires only simple and readily available reagents. Finally, no special technical expertise is required in the performance of the FSI-test and accordingly it can be employed in a relatively unsophisticated environment.

The subject test fulfills an important need in allowing for a simple, reliable, and rapid test for the determination of fetal pulmonary maturity. In particular, test kits can be provided which allow for accurate measurement of the reagents, so as to minimize variations due to the technician's or operator's measurement of volumes. Furthermore, by allowing for standard comparisons, the technician is more readily able to evaluate positive and negative results, lowering the degree of potential for misreading the result.

Although the foregoing invention has been described in some detail by way of illustration and example for purposes of clarity of understanding, it will be obvious that certain changes and modifications may be practiced within the scope of the appended claims.

What is claimed is:

1. A method for measuring fetal or neonatal lung maturity employing amniotic fluid comprising:

combining a predetermined volume of amniotic fluid with graduated amounts of 95% aqueous ethanol to 100% ethanol to provide at least six mixtures of graduated ethanol volume fractions from 0.45 to 0.50 to 0.01 graduations;

agitating each of the mixtures in substantially the same manner; and determining the highest ethanol volume fraction which results in a persistent foam at the interface;

wherein an ethanol volume fraction of greater than 0.45 with persistent foam indicates fetal lung maturity.

2. A method according to claim 1, wherein a small amount of dye is introduced into said ethanol.

3. A method according to claim 1, wherein negative and positive controls are employed for comparison of said mixtures with said controls.

4. A kit for use in the method according to claim 1, containing six vials, each of the vials containing different amounts of 95% aqueous ethanol to 100% ethanol, so that upon admixture with a fixed amount of amniotic fluid, the vials provide ethanol volume fractions ranging from 0.45 to 0.50 at 0.01 graduations.

5. A kit according to claim 4, where included in said ethanol is a small amount of a dye.

6. A kit according to any of claims 4 or 5, including two additional vials, one vial containing 40 microg. dipalmitoyl lecithin, 377 microl. of ethanol and 500 microl. of saline as a positive control, and 20 microg. of dipalmitolyl lechthin, 500 microl. of ethanol and 500 microl. of saline as a negative control.

* * * * *